(12) United States Patent
Zheng

(10) Patent No.: US 10,064,780 B2
(45) Date of Patent: Sep. 4, 2018

(54) MULTI-FUNCTIONAL ACTIVITY MANAGEMENT SYSTEM FOR ELDERLY

(71) Applicant: Beijing Rongchuangyuanda Network Technology Co., LTD., Beijing (CN)

(72) Inventor: Zhongshu Zheng, Beijing (CN)

(73) Assignee: GUANGZHOU YUNLANG INFORMATION TECHNOLOGY CO., LTD., Guangzhou, Guangdong Province (CN)

( * ) Notice: Subject to any disclaimer, the term of this patent is extended or adjusted under 35 U.S.C. 154(b) by 0 days.

(21) Appl. No.: 15/396,418

(22) Filed: Dec. 30, 2016

(65) Prior Publication Data

US 2018/0177266 A1    Jun. 28, 2018

(30) Foreign Application Priority Data

Dec. 27, 2016 (CN) .......................... 2016 1 1227476

(51) Int. Cl.
| | |
|---|---|
| *A61H 3/00* | (2006.01) |
| *A61H 3/06* | (2006.01) |
| *A45B 3/02* | (2006.01) |
| *A45B 9/02* | (2006.01) |
| *A45B 21/00* | (2006.01) |
| *H04B 1/034* | (2006.01) |
| *H04W 4/02* | (2018.01) |
| *A45B 9/00* | (2006.01) |

(52) U.S. Cl.
CPC .................. *A61H 3/00* (2013.01); *A45B 3/02* (2013.01); *A45B 9/02* (2013.01); *A45B 21/00* (2013.01); *A61H 3/06* (2013.01); *A45B 2009/002* (2013.01); *A45B 2009/005* (2013.01); *H04B 1/0346* (2013.01); *H04M 2250/10* (2013.01); *H04W 4/023* (2013.01)

(58) Field of Classification Search
CPC ....................................................... A61H 3/06
See application file for complete search history.

(56) References Cited

U.S. PATENT DOCUMENTS

| | | | | |
|---|---|---|---|---|
| 629,460 | A * | 7/1899 | Nagell .................... | A45B 21/00 135/17 |
| 661,990 | A * | 11/1900 | Hubendubel .......... | A45B 21/00 135/18 |
| 1,843,290 | A * | 2/1932 | Maxwell, Jr. .......... | A45B 21/00 135/17 |
| 5,470,233 | A * | 11/1995 | Fruchterman .... | G08G 1/096861 340/4.14 |
| 6,356,210 | B1 * | 3/2002 | Ellis ....................... | A61H 3/061 135/67 |
| 6,774,795 | B2 * | 8/2004 | Eshelman ............ | A61B 5/0002 340/539.1 |

(Continued)

*Primary Examiner* — David R Dunn
*Assistant Examiner* — Danielle Jackson
(74) *Attorney, Agent, or Firm* — Cheng-Ju Chiang

(57) ABSTRACT

A multi-functional activity management system for elderly utilizes prior art walking sticks to manage big data related to activity of elderly persons. In addition, new improvements have been made upon prior art walking sticks. By incorporating umbrella function into the walking stick, the stem portion becomes narrower and shorter, thereby making it easy to be inserted into the thin walking stick. New functions have been developed from the prior art walking sticks for better use by the elderly persons.

6 Claims, 3 Drawing Sheets

(56) References Cited

U.S. PATENT DOCUMENTS

| | | | | |
|---|---|---|---|---|
| 7,654,275 B2* | 2/2010 | Ewell | ............... | A45B 3/00 |
| | | | | 135/66 |
| 8,397,737 B2* | 3/2013 | Evans | ............... | A45B 9/00 |
| | | | | 135/65 |
| 9,322,657 B2* | 4/2016 | Friedlander | ............ | G01C 21/00 |
| 9,386,830 B2* | 7/2016 | Crowhurst | ............... | A45B 9/00 |
| 9,513,126 B2* | 12/2016 | Sun | ............... | G01C 21/005 |
| 9,618,624 B2* | 4/2017 | Krauss | ............... | A45B 3/08 |
| 2008/0072940 A1* | 3/2008 | Cheng | ............... | A45B 3/00 |
| | | | | 135/66 |
| 2008/0251110 A1* | 10/2008 | Pede | ............... | A61H 3/061 |
| | | | | 135/66 |
| 2009/0223546 A1* | 9/2009 | Nazarian | ............... | A45B 3/04 |
| | | | | 135/66 |
| 2016/0030275 A1* | 2/2016 | Liang | ............... | A61H 3/061 |
| | | | | 701/491 |
| 2016/0262661 A1* | 9/2016 | Sarkar | ............... | A61B 5/112 |
| 2017/0006981 A1* | 1/2017 | Samson | ............... | A45B 3/00 |

* cited by examiner

MULTI-FUNCTIONAL ACTIVITY MANAGEMENT SYSTEM FOR ELDERLY

FIELD OF THE INVENTION

The present disclosure relates to a big data management system and more particularly, to a multi-functional activity management system for elderly.

BACKGROUND OF THE INVENTION

Currently in China, it comes time of a large population of elderly persons. On one hand, it has become a critical issue on how to effectively provide service to elderly through big data. On the other hand, there are increasing needs of elderly-related products with various functions. Walking sticks used by elderly in their everyday life only have a single function and therefore no longer meet requirements of elderly. Though kinds of novel walking sticks are seen in the marketplace, they are only combination of kinds of separate products. These combined walking sticks fail to comply with situations of actual production and usage. They are inconvenient in use and operation for elderly.

SUMMARY OF THE INVENTION

The technical problem to be solved by the current invention is to provide a multi-functional activity management system for elderly for real time collecting and monitoring big data related to activities of elderly such that the elderly can conveniently use and operate the system.

To solve the above-mentioned technical problem, the following technical solution is proposed.

A multi-functional activity management system for elderly includes a plurality of walking stick activity data-collecting terminals and a data management center.

Each walking stick activity data-collecting terminal comprises a handle and a stem portion; a positioning module, an activity data collection module, and an activity data transmission module are disposed inside the handle.

The positioning module is configured to track geographical location of the elderly in real time;

The activity data collection module is configured to collect information of current geographical location of the elderly.

The activity data transmission module is configured to transmit the information of current geographical location of the elderly to the data management center.

The data management center includes an activity data receiving module for receiving information of geographical location of the elderly sent from respective walking stick activity data-collecting terminals; and an activity data processing module for determining big data information of activity of elderly according to geographical location information of respective elderly, and for analyzing and thereby obtaining activity data of elderly using said big data information of activity of elderly.

Preferably, the positioning module is realized by GPS or mobile base station information.

Preferably, the activity data of elderly comprises spots where an elderly person frequently goes and traveling lines along which an elderly person often walks.

Preferably, for each walking stick activity data-collecting terminal, a top end of the stem portion is opened and recessed downwardly to form a first receiving chamber; a plurality of holding holes are defined evenly circumferentially in the stem portion at its top end; a downwardly faced second receiving chamber is defined in the handle at a location where the handle is connected to the stem portion;

a plurality of spherical embossments are extended from an inner wall of the second receiving chamber;

a plurality of guiding grooves is defined in the inner wall of the first receiving chamber; a closed umbrella face is formed in the first receiving chamber along said guiding grooves; the umbrella face has an umbrella face rod; a lower end of the rod is provided with a number of resilient hooks; When the umbrella face is to be opened, the resilient hooks on the lower end of the umbrella face rod are inserted into corresponding holding holes to form a bottom support of the umbrella face; and when the face is to be folded, the umbrella face is guided by the guiding grooves and received into the first receiving chamber, and the spherical embossments on the inner wall of the second receiving chamber of the handle of the walking stick are located into corresponding holding holes to form an integral walking stick.

Preferably, a bottom of the first receiving chamber is a V-shaped or U-shaped bottom; and the downmost portion of the V-shaped or U-shaped bottom is provided with a draining hole communicated with outside environment.

Preferably, a lighting lamp is disposed at a front end of the handle, and a switch for the lamp is disposed on a rear end of the handle.

Preferably, the number of the spherical embossments is less than that of the holding holes, and there are same numbers of resilient hooks and holding holes.

Correspondingly, also proposed is a walking stick activity data-collecting terminal, which includes a handle and a stem portion.

A positioning module, an activity data collection module, and an activity data transmission module are disposed inside the handle.

The positioning module is configured to track geographical location of the elderly in real time.

The activity data collection module is configured to collect information of current geographical location of the elderly.

The activity data transmission module is configured to transmit the information of current geographical location of the elderly to a data management center.

Preferably, the positioning module is realized by GPS or mobile base station information.

A top end of the stem portion is opened and recessed downwardly to form a first receiving chamber; a plurality of holding holes are defined evenly circumferentially in the stem portion at its top end; a downwardly faced second receiving chamber is defined in the handle at a location where the handle is connected to the stem portion.

A plurality of spherical embossments is extended from an inner wall of the second receiving chamber.

A plurality of guiding grooves is defined in the inner wall of the first receiving chamber; an umbrella face which be closed is formed in the first receiving chamber along said guiding grooves; the umbrella face has an umbrella face rod; a lower end of the rod is provided with a number of resilient hooks; When the umbrella face is to be opened, the resilient hooks on the lower end of the umbrella face rod are inserted into corresponding holding holes to form a bottom support of the umbrella face; and when the face is to be folded, the umbrella face is guided by the guiding grooves and received into the first receiving chamber, and the spherical embossments on the inner wall of the second receiving chamber of the handle of the walking stick are located into corresponding holding holes to form an integral walking stick.

Compared with prior art, the current invention brings the following good effects.

The multi-functional activity management system for elderly of the invention utilizes prior art walking sticks to manage big data related to activity of elderly persons. A number of walking stick activity data-collecting terminals collect activity big data information of the elderly persons. The information is then analyzed by the data management center to obtain elderly activity regular data, thus realizing providing effective services to elderly persons.

In addition, new functions are developed from prior art walking sticks. In other words, a top end of the stem portion is opened and recessed downwardly to form a first receiving chamber; a plurality of holding holes are defined evenly circumferentially in the stem portion at its top end; and a downwardly faced second receiving chamber is defined in the handle at a location where the handle is connected to the stem portion. A plurality of spherical embossments is extended from an inner wall of the second receiving chamber.

A plurality of guiding grooves is defined in the inner wall of the first receiving chamber; an umbrella face which be closed is formed in the first receiving chamber along said guiding grooves; the umbrella face has an umbrella face rod; a lower end of the rod is provided with a number of resilient hooks; When the umbrella face is to be opened, the resilient hooks on the lower end of the umbrella face rod are inserted into corresponding holding holes to form a bottom support of the umbrella face; and when the umbrella face is to be folded, the umbrella face is guided by the guiding grooves and received into the first receiving chamber, and the spherical embossments on the inner wall of the second receiving chamber of the handle of the walking stick are located into corresponding holding holes to form an integral walking stick. Using this structure, only part of the entire length of the stem portion corresponding to the umbrella face is required to be contained in the first receiving chamber without need of inserting the whole length of the stem portion. In other words, the length of the stem portion is only required to extend to the umbrella face. Moreover, as only the stem portion with the length of the umbrella face is utilized, there is no need of contractive stem portion. As such, the stem portion becomes narrower and shorter, thereby making it easy to be inserted into the thin walking stick.

DETAILED DESCRIPTION OF THE INVENTION

Figure 1:
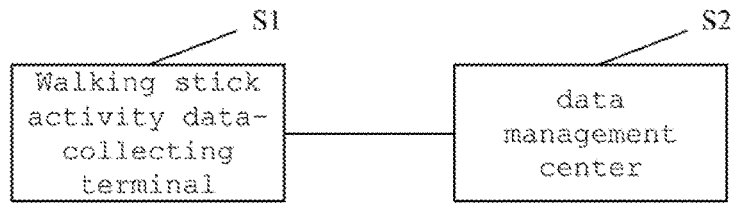
FIG. 1 shows a block diagram of a multi-functional activity management system for elderly in accordance with an embodiment of the invention.

With reference to FIG. 1 showing a block diagram of a multi-functional activity management system for elderly in accordance with an embodiment of the invention, the multi-functional activity management system for elderly includes a plurality of walking stick activity data-collecting terminals S1 and a data management center S2. Specifically, this is realized by normally available walking stick and therefore, it can be used by elderly with convenience. To realize activity data collection, each walking stick activity data-collecting terminal S1 in this embodiment includes a handle 1 and a stem portion 2. Inside the handle 1 are a positioning module S11, an activity data collection module S12, and an activity data transmission module S13. Here, the positioning module S11 tracks geographical location of the elderly in real time and this can be embodied by GPS or mobile base station information or the like. Detailed description thereof is omitted herefrom.

The activity data collection module S12 collects information of current geographical location of the elderly.

The activity data transmission module S13 transmits the information of current geographical location of the elderly to the data management center S2.

Figure 3:
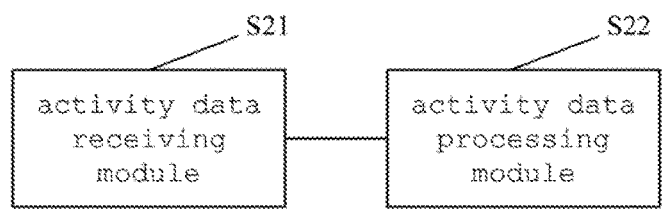
FIG. 3 denotes structure of a data management center of the multi-functional activity management system in accordance with an embodiment of the invention.

In addition, referring also to FIG. 3, the data management center S2 in this embodiment may include an activity data receiving module S21 for receiving information of geographical location of the elderly sent from respective walking stick activity data-collecting terminals S1; and an activity data processing module S22 for determining big data information of activity of elderly according to geographical location information of respective elderly, and for analyzing and thereby obtaining activity data of elderly using said big data information of activity of elderly. Specifically, the activity data of elderly obtained by analyzing the big data information of activity may include spots where an elderly person frequently go and traveling lines along which an elderly person often walks and the like.

Figure 4:
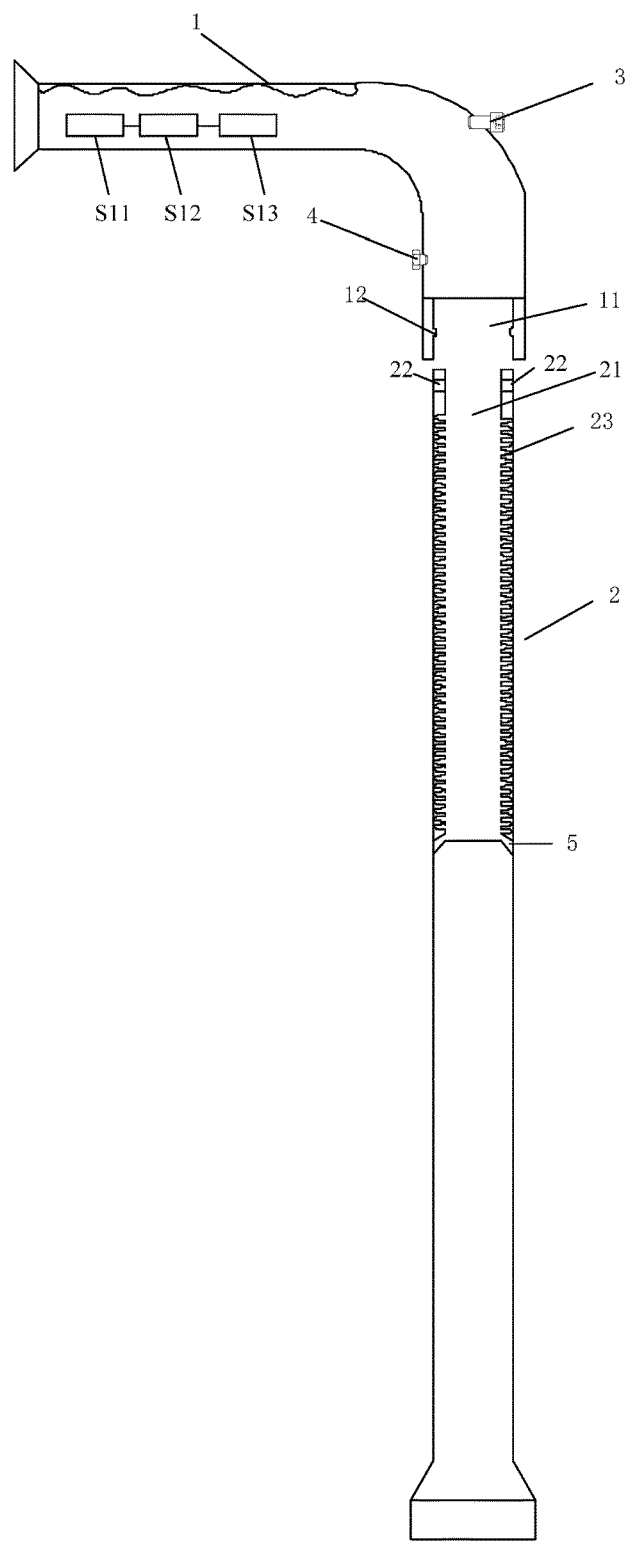
FIG. 4 depicts a mechanical construction of the walking stick activity data-collecting terminal of the multi-functional activity management system of the invention.
Figure 5:
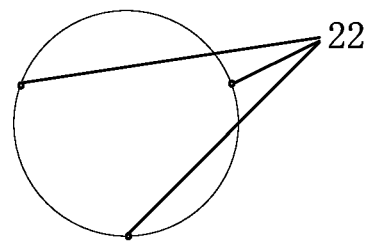
FIG. 5 shows distribution of a plurality of holding holes of the walking stick activity data-collecting terminal of the multi-functional activity management system of the invention.
Figure 6:
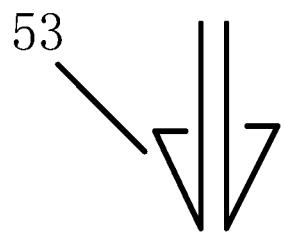
FIG. 6 shows detailed structure of a resilient hook of the walking stick activity data-collecting terminal of the multi-functional activity management system of the invention.

Moreover, to facilitate operation of the walking stick activity data-collecting terminals, in this embodiment, similar improvements have been made upon prior art walking sticks. As shown in FIGS. 4-6, a multi-functional activity management system for elderly according to this embodiment includes a handle 1 and a stem portion 2. A top end of the stem portion 2 is opened and recessed downwardly to form a first receiving chamber 21. A plurality of holding holes 22 are defined circumferentially in the stem portion 2 at its top end. A downwardly faced second receiving chamber 11 is defined in the handle 1 at a location where the handle 1 is connected to the stem portion 2. A plurality of spherical embossments 12 are extended from an inner wall of the second receiving chamber 11.

In general, when folding an umbrella face or putting it into an umbrella bag, normally it requires patience for a person to sequentially fold these faces and it also takes time. The umbrella face will be irregular and it will be difficult to place the umbrella into the bag if operation is wrong especially for elderly persons who have weak eyesight and vigor. To avoid this problem, in this embodiment, a plurality of guiding grooves 23 may be defined in the inner wall of the first receiving chamber 21. In particular, inner threads may be used as said guiding grooves. A closed umbrella face is formed in the first receiving chamber 21 along said guiding grooves 23. By this manner, when the umbrella face is placed into the first receiving chamber 21, the umbrella face can be guided by the guiding grooves 23 in a clockwise or counter clockwise direction and then be folded. This operation is simple and convenient. Furthermore, different from prior art techniques, in this embodiment, the umbrella face has an umbrella face rod. A lower end of the rod is provided with a number of resilient hooks 53 (See FIG. 6). When the umbrella face is to be opened, i.e., when the umbrella face is to be pulled out, the resilient hooks 53 on the lower end of the umbrella face rod will move upwardly with the umbrella face. When the hooks 53 move to the corresponding holding holes, the hooks 53 will be resiliently expanded and inserted into corresponding holding holes to form a bottom support of the umbrella face. When the umbrella face is to be folded, the resilient hooks 53 are compressed to contract inwardly and then are contained in the first receiving chamber together with the umbrella face. The spherical embossments on the inner wall of the second receiving chamber of the handle of the walking stick are located into corresponding holding holes to form an integral walking stick.

It is noted that rainwater may remain inside the stick when the umbrella is contained in the stick. To quick get rid of rainwater, in this embodiment, a bottom of the first receiving chamber 11 may be a V-shaped or U-shaped bottom. In addition, the downmost portion of the V-shaped or U-shaped bottom is provided with a draining hole 5 communicated with outside environment.

Figure 2:
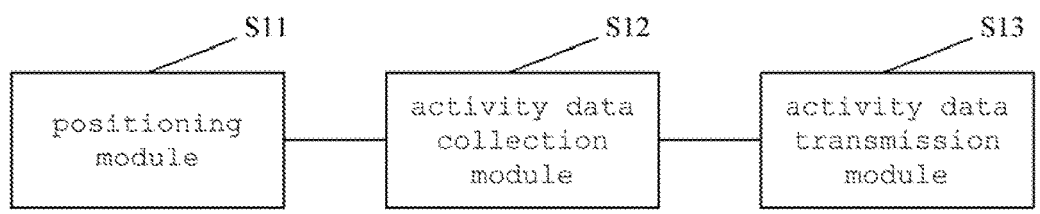
FIG. 2 shows a functional block diagram illustrating activity data collection performed by a walking stick activity data-collecting terminal of the multi-functional activity management system of the invention.

Furthermore, in this embodiment, when connecting the handle 1 and stem portion 2, the number of the spherical embossments may be less than that of the holding holes. It is preferable that there are same number of resilient hooks and holding holes to better support the umbrella faces. Specifically, there may be 3 holding holes. For example as shown in FIG. 2, there are 3 holding holes evenly distributed on the circumference of the top of the stem portion 2. In fact, 4 or more holding holes are also possible.

In addition, the elderly often has weak eyesight, to help him see the road clearly in darker environment, the functions of the walking stick may be further enhanced. For instance, a lighting lamp 3 may be disposed at a front end of the handle 1, and correspondingly, a switch 4 for the lamp 3 may be disposed on a rear end of the handle 1.

Finally, it is emphasized that the above description is only for preferred embodiments of the invention but not to limit the scope of the invention. Any equivalent of or modification upon the invention are within the scope of the invention.

What is claimed is:

1. A multi-functional activity management system for elderly, comprising a plurality of walking stick activity data-collecting terminals and a data management center; wherein
    each walking stick activity data-collecting terminal comprises a handle and a stem portion; a positioning module, an activity data collection module, and an activity data transmission module are disposed inside the handle;
    the positioning module is configured to track geographical location of the elderly in real time;
    the activity data collection module is configured to collect information of current geographical location of the elderly;
    the activity data transmission module is configured to transmit the information of current geographical location of the elderly to the data management center;
    the data management center comprises an activity data receiving module for receiving information of geographical location of the elderly sent from respective walking stick activity data-collecting terminals; and an activity data processing module for determining data information of activity of elderly according to geographical location information of respective elderly, and for analyzing and thereby obtaining activity data of elderly using said data information of activity of elderly;
    wherein for each walking stick activity data-collecting terminal:
    a top end of the stem portion is opened and recessed downwardly to form a first receiving chamber; a plurality of holding holes are defined evenly circumferentially in the stem portion at its top end; a downwardly faced second receiving chamber is defined in the handle at a location where the handle is connected to the stem portion;
    a plurality of spherical embossments are extended from an inner wall of the second receiving chamber; and the spherical embossments on the inner wall of the second receiving chamber of the handle of the walking stick are located into corresponding holding holes to form an integral walking stick;
    a plurality of guiding grooves are defined in the inner wall of the first receiving chamber;
    and the spherical embossments on the inner wall of the second receiving chamber of the handle of the walking stick are located into corresponding holding holes to form an integral walking stick;
    wherein a bottom of the first receiving chamber is a V-shaped or U-shaped bottom; and the downmost portion of the V-shaped or U-shaped bottom is provided with a draining hole communicated with outside environment.

2. The system as recited in claim 1, wherein the positioning module is realized by GPS or mobile base station information.

3. The system as recited in claim 1, wherein the activity data of elderly comprises spots where an elderly person frequently go and traveling lines along which an elderly person often walks.

4. The system as recited in claim 1, wherein a lighting lamp is disposed at a front end of the handle, and a switch for the lamp is disposed on a rear end of the handle.

5. A walking stick activity data-collecting terminal comprising: a handle and a stem portion;
    wherein a positioning module, an activity data collection module, and an activity data transmission module are disposed inside the handle;
    the positioning module is configured to track geographical location of the elderly in real time;
    the activity data collection module is configured to collect information of current geographical location of the elderly; and
    the activity data transmission module is configured to transmit the information of current geographical location of the elderly to a data management center;
    a top end of the stem portion is opened and recessed downwardly to form a first receiving chamber; a plurality of holding holes are defined evenly circumferentially in the stem portion at its top end; a downwardly faced second receiving chamber is defined in the handle at a location where the handle is connected to the stem portion;

a plurality of spherical embossments are extended from an inner wall of the second receiving chamber; and the spherical embossments on the inner wall of the second receiving chamber of the handle of the walking stick are located into corresponding holding holes to form an integral walking stick;

a plurality of guiding grooves are defined in the inner wall of the first receiving chamber;

wherein a bottom of the first receiving chamber is a V-shaped or U-shaped bottom; and the downmost portion of the V-shaped or U-shaped bottom is provided with a draining hole communicated with outside environment.

6. The terminal as recited in claim 5, wherein the positioning module is realized by GPS or mobile base station information.

* * * * *